United States Patent

Holmgren et al.

[11] Patent Number: 5,936,503
[45] Date of Patent: Aug. 10, 1999

[54] CONTROLLABLE INDUCTOR

[75] Inventors: Tommy Holmgren; Björn Sandin, both of Ludvika; Stefan Valdemarsson, Västerås; Dan Elofsson, Ludvika, all of Sweden

[73] Assignee: Asea Brown Boveri AB, Vasteras, Sweden

[21] Appl. No.: 08/896,499

[22] Filed: Jul. 18, 1997

[51] Int. Cl.[6] .............................. H01F 27/08; H01F 27/02
[52] U.S. Cl. .................................... 336/60; 336/59; 336/55
[58] Field of Search .................................. 336/55, 60, 57, 336/59

[56] References Cited

U.S. PATENT DOCUMENTS

| | | |
|---|---|---|
| 1,304,257 | 5/1919 | Brand . |
| 2,459,322 | 1/1949 | Johnston .................................. 175/316 |
| 2,751,562 | 6/1956 | Camilli et al. ............................. 336/60 |
| 2,942,213 | 6/1960 | Camilli et al. ............................. 336/60 |
| 3,775,719 | 11/1973 | Gainer et al. ............................. 336/58 |

*Primary Examiner*—Renee S. Luebke
*Assistant Examiner*—Anh Mai
*Attorney, Agent, or Firm*—Watson Cole Grindle Watson P.L.L.C.

[57] ABSTRACT

A controllable inductor including a tubular core, a main winding (1) surrounding the core, a control winding running substantially axially to the core and an element (3) surrounding the core and arranged to support the main winding wound outside thereof in radial layers. The element includes means arranged to provide channels (19) partly defined by the radially inner turn of the main winding. Said channels are communicating with spacings between said layers (2). A member is arranged to generate a flow of air in the channels and through the spacings of the layers for cooling the main winding.

14 Claims, 3 Drawing Sheets

CONTROLLABLE INDUCTOR

FIELD OF THE INVENTION AND PRIOR ART

The present invention relates to a controllable inductor including at least one tubular core, a main winding surrounding the core, a control winding running substantially axially through the core and returning substantially axially outside thereof and an element surrounding the core and arranged to support the main winding wound outside thereof in radial layers with respect to the core, said layers being created by a plurality of turns of a conductor wound outside onto each other and running successively in axial direction with axial spacings between successive layers, wherein a member is arranged in the proximity of one of the axial ends of the core for generating a flow of air passing the control winding and the core for cooling thereof.

Such a controllable inductor is previously known from, for example, the applicant's WO 94/11891. The definition of "controllable" is to be given such a wide meaning, that it also comprises the case that a control current which is constant over time passes through the control winding.

A controllable inductor of this type functions in conjunction with a capacitor as a so-called harmonic filter in connection with a high voltage station for converting direct voltage to alternating voltage and vice versa, wherein its main winding is connected to the high voltage net over a capacitor, usually on the alternating voltage side.

In such a controllable inductor the permeability of its core and thereby the inductance is adjusted with the aid of the cross-magnetization generated inside the core by usually causing direct current to run through said control winding, but the current may be alternating current as well, wherein the inductance of the inductor may be adjusted to exactly that frequency an overtone generated in the high voltage net is having for an effective fade-out thereof while causing small energy losses in the inductor.

It is a task to produce inductors of this type as compact as possible, while in this way space and especially considerable costs may be saved, especially for the material that the inductor is built of. Thereby it is also important that the core may store as much energy as possible, wherein the energy is proportional to the square of the flux density of the longitudinal flow through the core generated from the alternating (in most cases) voltage over the main winding and inversely proportional to the permeability of the core. For achieving a low permeability it is important to achieve the highest possible number of ampere-turns of the control winding through the core. When the task is to achieve a compact inductor the spacings between the control windings should be as small as possible, which requires that flows of air are forced to pass the control winding and the core for cooling thereof. Because of the cross-magnetization achieved in the core by the current through the control winding, the hysteresis losses will be almost eliminated in the core, but in spite of different arrangements to decrease the eddy current losses in the core, such as winding the core in a plurality of turns of thin sheet metals as well as dividing the core in core rings mutually insulated and stacked on top of each other, it will be necessary to cool the core by forcing flows of air past it to achieve the task of the more compact inductor.

A new controllable inductor produced by the present inventors was possible to form considerably more compact than such controllable inductors previously known especially in axial direction thanks to measures, which bring the eddy current losses in the core down as well as improvements of the maximum ampere turns of the control winding at a given winding room This implies that the way the main winding previously has been applied, i.e. lying directly on top of said element with a minority of turns of winding per layer and large axial spacings between the layers, is not possible anymore. The heat release taking place through the current flow in the main winding has thus suddenly become a problem, since a larger number of windings must be applied per layer and the layers must be arranged considerably closer to each other than before for adaption to the more compact core. Thus, this implies a risk of limiting how compact the core may be formed, which would be of great disadvantage.

SUMMARY OF THE INVENTION

The object of the present invention is to provide a controllable inductor of the type defined in the introduction, which solves the above mentioned problems of the limiting effect of the main winding upon how compact the inductor might be made.

This object is achieved according to the invention by way of providing said element of such a controllable inductor with means arranged to provide channels communicating with said spacings from one end of the main winding, as seen axially, to the other end thereof and extending substantially axially and partially defined by the radially inner turn of the main winding and by arranging a member to generate a flow of air in these channels and through said spacings for cooling the main winding.

Thanks to the arrangement of said channels and said members for generating a flow of air through these and through the spacings between successive layers of the main winding, it becomes possible to both arrange a larger number of turns of winding per layer, and to make the distance between two successive layers smaller than previously has been possible, so that the heat release of the main winding not will limit how compact the inductor may be made in axial direction.

According to a preferred embodiment; of the invention said element has outer wall surfaces arranged to define said channels inside as seen radially. Because the element supporting the main winding in this way is utilized to provide said channels this may be done in an easy and inexpensive way.

According to another preferred embodiment of the invention said means comprises members arranged to hold the layers of the main winding at a radial distance from the walls of the element for defining air channels between outer wall surfaces of the element and inner turns of the main winding This construction is easy and effective and the main winding will be effectively cooled by the flow of air passing it inside the channel and thanks to said layer spacings by air that will flow in these spacings between the channels and the outside.

According to another preferred embodiment of the invention said holding members are projecting from the element and distributed around the circumference of the element with at circumferencial distances forming circumferencial spacings, so that axially spacings free for air passage are formed between adjacent layers in said circumferencial spacings. In this way it is possible to pack the layers of the main winding so closely together that respective holding member will bear on both an upper and a lower winding layer, and yet achieve free spacings between these layers. This fact makes it possible to arrange the holding members to protrude between successive radial layers of the main winding and function as a distance element between these, so that the axial distance between two successive layers corresponds to the thickness of said holding member in the axial direction, which forms a further preferred embodiment of the invention.

According to another preferred embodiment of the invention said means comprises members arranged outside said element and arranged to form radial supports for the innermost turn of each layer of the main winding at a distance from the element. Thanks to the arrangement of such radial supports it is possible to easily hold the main winding in place at a distance from said element for enabling good cooling.

According to another preferred embodiment of the invention said member for generating a flow of air through said channels has been arranged in the proximity of a second end of the element at an inductor where said main winding is wound from a first end intended to be connected to a high potential in a first radial layer from the inside and outwardly or from the outside and inwardly and thereafter gradually to said second end of the element, where it is intended to be connected to ground potential, from the inside and outwardly each second time and from the outside and inwardly each second time in turn layer by layer. This position for arranging said member is advantageous, as the screen-off between the main winding and components located inside it of the inductor is not as important at this end as at the other end and the measures for connecting said channels with said member generating the flow of air will thus be considerably easier.

According to another preferred embodiment of the present invention said element is formed by an electrically insulating material and arranged to electrically screen off components of the inductor located radially inside thereof relative said main winding, a closed room is formed inside said element axially at said first end, and said element has openings adjacent to said second end for air communication between said room located inside said element and said air channels running outside said element. Because the room inside said element is made closed at the first end and openings are arranged in the element at the second end between this room and the air-channels, the member generating the flow of air may effectively force a flow of air to flow between said room and said channels.

According to another preferred embodiment of the invention said member for generating a flow of air in said channels is arranged to force air through said channels and said layer spacings. It has been noted that the best cooling effect is achieved in this way, wherein the effectiveness will be especially high when the air that is forced into said room only may deviate therefrom by way of flowing out in the channels.

According to another preferred embodiment of the invention the same member is arranged to generate a flow of air passing said control winding and said core for cooling thereof and at the same time in said channels for cooling said main winding. By this way of utilizing the member that yet is located there for cooling the control winding and the core to also cool the main winding, the construction of the inductor will naturally be simplified, and this solution is advantageous both regarding the lesser room demandings and its low costs According to another preferred embodiment of the invention, the member for generating a flow of air through said channels is arranged substantially centrally at one end of the inductor, which results in good conditions for utilizing only one member for achieving cooling of both the control winding and the core as well as the main winding and which easily makes it possible to reach all the surfaces that are to be cooled with the cooling air.

Further advantages and advantageous characteristics of the invention will be apparent from the following description and the other depending claims

BRIEF DESCRIPTIONS OF THE DRAWINGS

With reference to the appended drawings, below follows a description of a preferred embodiment of the invention cited as an example In the drawings.

DETAILED DESCRIPTION OF A PREFERRED EMBODIMENT OF THE INVENTION

Figure 1:
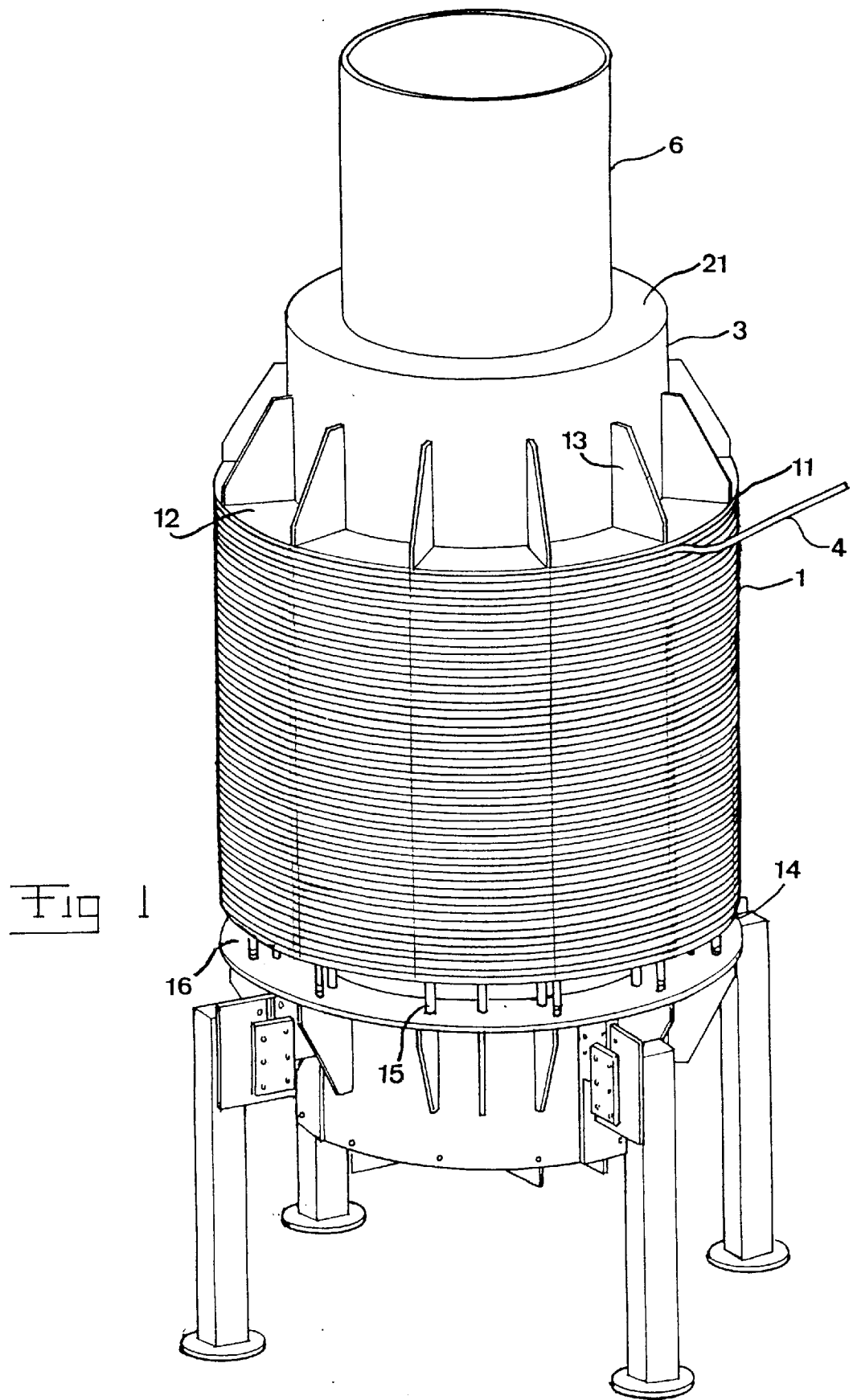
FIG. 1 shows in a perspective view an inductor according to a preferred embodiment of the invention.
Figure 2:
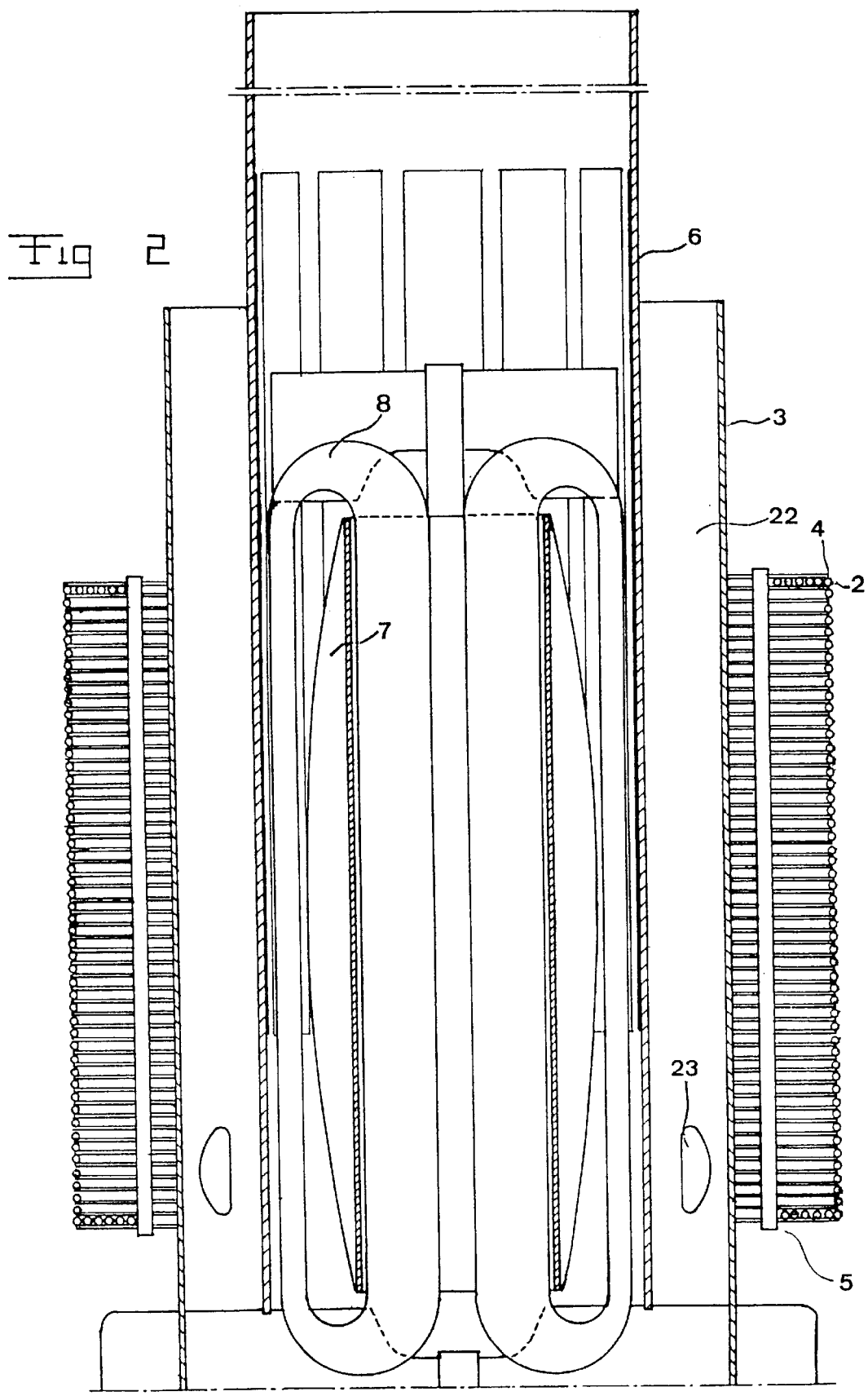
FIG. 2 shows in a partly cut, simplified view the general construction of said controllable inductor according to FIG. 1.

The general construction of a new controllable inductor with a very compact construction relative to previously known such inductors is illustrated in FIGS. 1 and 2, which controllable inductor is developed by the inventors in question. The compact construction, which has been enabled among other things by advantageous designs of the core of the inductor and the control winding as well as specific field control arrangements, which are objects of other patent applications and which will not be discussed here, since they have nothing else to do with the present invention except for them necessitating a closer arrangement of the main winding of the inductor, and the solution of the problem developed by the arised need for cooling of the main winding are what the present invention is aimed at. The controllable inductor has the following general construction. It has a main winding 1 intended to be connected to a high voltage net and which is formed by winding a conductor in a plurality of turns from inside and outwards and from outside and inwards in radial layers 2, running successively in axial direction. For simplifying reasons not all, but only the outer turns of the winding are shown on the drawing, except for the layers located at the ends. The winding is supported with respective inner turns of winding at a distance outside an element 3 and by the same in the form of a cylinder of electrically insulating material The main winding 1 has an end 4 located on a high voltage potential, wherein the voltage is falling in direction to the opposite lower end 5, shown in FIG. 2, which end is on ground potential A cylinder 6 consisting of electrically insulating material is arranged inside the cylinder 3 and co-axially thereto In the room defined by the cylinder 6 there is a core 7 arranged co-axially thereto, through which the longitudinal magnetic flux, generated by the high voltage in the main winding 1 passes. A control winding 8 is connectable to a direct current source for sending a direct current through same, which will generate a tangentially directed magnet flux in the core, which extends transversally with respect to the main flux and by this way decreases the permeability of the core for the longitudinal magnet flux from the main winding while the hysteresis loss in the core is almost eliminated. However, it would also be possible to utilize an alternating current as a control current in some cases. By increasing the control current the permeability of the core may be decreased and thereby the inductance of the inductor is also decreased. A lower permeability of the core also causes a larger storage capacity of energy per unit volume, so that the inductor may be made more compact.

Figure 3:
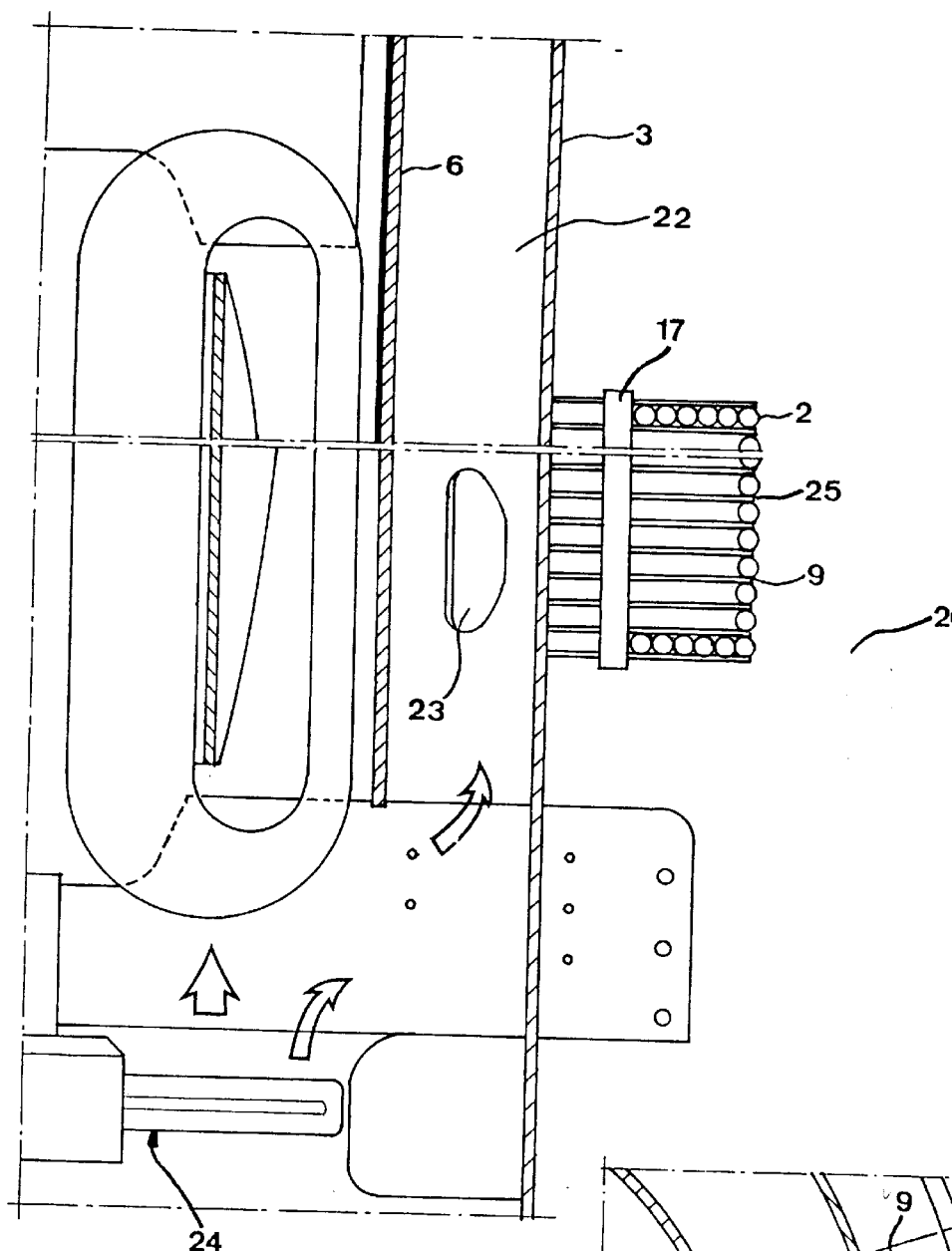
FIG. 3 shows in an enlarged, partly cut view relative to FIG. 2, one part of the inductor shown in FIGS. 1 and 2.
Figure 4:
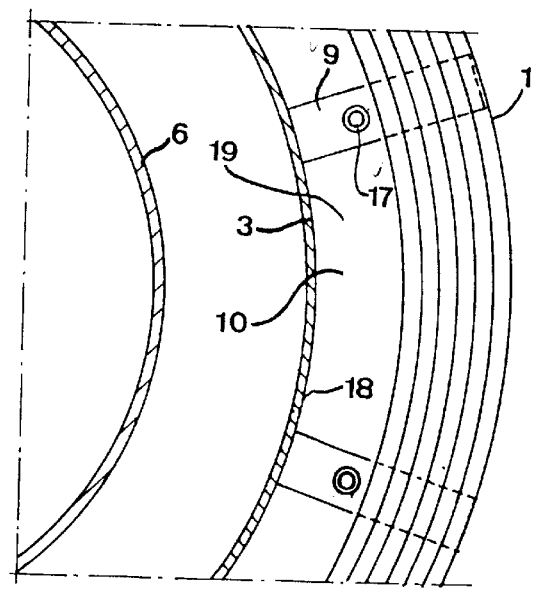
FIG. 4 shows in an enlarged view a portion of the inductor according to FIGS. 1 and 2 in a radial cross section

Heat is generated in said core, said control winding and said main winding due to the operation of the inductor and it will be described below how the cooling of these components takes place, wherein the present invention is especially directed to the cooling of the main winding Thus it will now also be referred to FIG. 3 and 4. The main winding is supported by holding members 9 in the form of relatively thin plates, which are protruding essentially radially from said cylinder 3. These holding members 9 are distributed around the circumference of said cylinder 3 with circumferencial spacings 10 forming circumferencial distances. Thereby the plates 9 are arranged to function as distance elements between successive radial layers of said main winding and their thickness thereby sets the "height" of said spacings existing between said layers in the areas (spacings 10) where no plate 9 is inserted. Above the uppermost winding layer 11 is a surrounding stop flange 12 secured to the cylinder 3 through consoles 13. A corresponding flange 14 is arranged at the other end of the winding below the lowest winding layer, wherein said inductor comprises members indicated at 15 for moving said lower flange 14 axially along said cylinder 3 for tightening of the main winding package against the stop flange 12. In this way it may be ensured that said main winding after the winding carried out thereof is transferred to a substantially rigid package with similar spacings between successive winding layers, which spacings are defined by the thickness of the holding members 9. The tightening members 15 are thereby supported by a fixedly arranged flange 16.

Said inductor also having members 17 in the form of bars, for forming radial support for the innermost winding of respective layer 2 to hold this at a distance from the outer wall 18 of cylinder 3. Said bars 17 are extending substantially axially through said plates 9, and thus arranged at the same angular distance around said element 3 as said holding members 9. Said holding members 9 and said support members 17 are thus cooperating for forming channels 19 free for air passage, which channels are defined inwardly by the outer wall 18 of said element and outwardly by the main winding. These channels 19 are communicating with the outside 20 through the spacings the holding members 9 are causing between successive winding layers 2, wherein these channels may be regarded having a cross section defined by holding members 9 adjacent in circumferencial direction, although they are mutually open. In this way there will be provided a path for cooling air passing the different turns of the main winding.

Said element 3 is ended on the upper side by a connecting roof 21, which is air-tightly connected to said cylinder 6. An axially closed room 22 will thereby be formed between said element 3 and said cylinder 6 at this end of said element. Adjacent to the other end 15 of said main winding openings 23 are performed through said element 3 in a way that said room 22 may communicate with said channels 19. These openings 23 are uniformly distributed around the circumference of said element. Such openings may not be arranged any higher due to insulating reasons. Said inductor having further a member 24 arranged substantially centrally at its lower end, which member is generating a flow of air and formed by a fan arranged with its exhaust side directed against said inductor, i.e. upwards, to draw in air from the region below said inductor and force this air on one hand through the cooling slots inside the inner cylinder 6 between its inner wall, said core and said control winding for cooling said control winding and said core, on the other into said room 22 where the air will be forced out through the openings 23 and into said channels 19 to flow upwards inside these channels between the outer wall 18 of the element and the inner turns of winding of the main winding and thereby gradually disappear to the outside by part air flows departing through the spacings between successive winding layers 2. In this way a good cooling of all turns of windings of said main winding will be achieved and this may occur with same air-flow-generating members which are effecting the cooling of said core and said control winding by forcing air through said inner cylinder 6 and out through the upper opening thereof.

Thanks to the effective cooling the distances between successive main winding layers 2 may be made small and each main winding layer may have relatively many turns of winding, wherein for exemplifying the thickness of said plates 9 could be x mm, the thickness of the conductors including insulation could be about y mm, wherein y is a multiple of x and the distance between the element and the innermost turn of each main winding layer is a multiple of y mm. The air-flow-generating member 24 is dimensioned and formed in a way that the lowest acceptable air speed through the spacings 25 between successive winding layers passing the turns of winding will be exceeded for all such spacings. As this air speed will decrease the further up against the first end 4 you get, there will be a considerably higher air speed at the lower parts compared to the upper parts. For example it would be possible that the air speed has to be forced to a speed of 4 m/s at the lower parts to be able to hold the speed above 0.5 m/s in the upper spacings between the layers.

The invention is of course not in any way limited to the preferred embodiment described above, but a number of possibilities to modifications thereof should be apparent to a man skilled in the art, without departing from the scope of the invention.

For example it would in principle, be possible to arrange a member that draws the air past the parts to be cooled but it has been noted, at least in the preferred embodiment described, that a considerably higher effectiveness is achieved when the air is forced past the parts to be cooled.

Further, it would of course be possible to form the element 3 open on the upper side and to arrange some sort of air-guiding members to guide the air from the air-flow-generating member into said channels.

The definition "channels" in the claims is to be seen in a wide perspective, and is by no means limited to that the channels must be laterally readingly defined, which by the way neither is the case in the embodiment shown. In principle, the definition covers all sorts of rooms allowing a movement of air passing therethrough and are at least partly defined by portions guiding the air in a specific direction. The plural declaration is also intended to comprise all numbers from one and more than one and thus also the case of a single surrounding open ring channel defined by the outer wall of the element and the winding layers.

The defined positions in the claims regarding the air-flow-generating member are to be seen in a way that it also could be arranged at another place instead of adjacent to one end of the inductor, and still being arranged to have its impact adjacent said end by air-guiding members.

The fact that the winding is formed from the inside and outwards is of course depending on how you look at it, and in all cases it could as well have been constructed from the outside and inwards.

With "high potential" all levels of voltage considerably higher than in the usual household electricity net are comprised and not only real high voltage. The invention is thus also directed to so-called intermediate voltage occurring for example in steel industry, the paper industry and in locomotive converting stations.

We claim:

1. A controllable inductor including at least one tubular core, a main winding surrounding the core having a central axis and first and second axial ends, a control winding running axially through the core and returning axially outside thereof and a support element surrounding the core for supporting the main winding, said main winding comprising a conductor radially wound about the outside of the support element in a plurality of successive, spaced apart, axially adjacent radial layers, the layers comprising a plurality of turns, each including an inner turn an outer turn and at least one intermediate turn of said conductor wound outwardly onto each other and running successively in an axial direction and having axial spacings between the successive layers, a member located proximate to one of the axial ends of the core for generating a flow of air through the control winding in the core, said support element including means providing air channels communicating with said spacings between the ends of the core, said support means extending axially and including a cylindrical wall surrounding the core; a plurality of elongated spacer members between each layer, said spacer members grouped in spaced apart planes corresponding to the spaces between successive layers of turns, each spacer member having a proximal end secured to the cylindrical wall and a free end extending outwardly to the outer turn, said spaced apart layers defining the air channels between the layers; an axially projecting holding member secured to each spacer member and located radially inward of the inner turn and spaced from the cylindrical wall for providing an annular air space therebetween partially defined by the radially inner turn of the main winding; and wherein said member located proximate to one end of the core generates a flow of air in the air channels through air channels and the annular space for cooling the main winding.

2. An inductor according to claim 1, wherein said element support includes a cylindrical outer wall.

3. An inductor according to claim 1, wherein each of said spacer members supports at least one of said holding members.

4. An inductor according to claim 1, wherein each of said spacer members is formed to extend axially at a distance from the cylindrical wall of the support element for forming radial supports for several adjacent main winding layers.

5. An inductor according to claim 4, wherein each of said spacer members is circumferentially distributed around the support element for radially supporting all the main winding layers.

6. An inductor according to claim 1, wherein said main winding is wound from the first end of the support element for connection to a high potential in one of the inner and outer turns and to the second end of the support element, for connection to ground potential, wherein said member for generating a flow of air through said channels is arranged in the proximity of said second end of the element.

7. An inductor according to claim 6, wherein said member for generating a flow of air in said channels forces the air from said second end through the channels towards said first end and partial streams thereof flow through said layer spacings.

8. An inductor according to claim 6, wherein said support element further comprises an electrically insulating material for electrically screening off an interior portion thereof with respect to said main winding, the interior an internal portion of said cylindrical wall being closed axially at said first end and having a plurality of openings adjacent to said second end for air communication between said interior portion and said air channels outside said core.

9. An inductor according to claim 8, wherein said member for generating a flow of air in said channels produces said flow of air through said openings between said interior and said channels.

10. An inductor according to claim 1, wherein the member generates a flow of air passing said control winding and said core for cooling thereof and at the same time in said channels for cooling said main winding.

11. An inductor according to claim 1, wherein said member for generating a flow of air in said channels forces air through the channels and said layer spacings.

12. An inductor according to any claim 1, wherein said member for generating a flow of air through said channels is located centrally at one end of the inductor.

13. A controllable inductor including at least one tubular core, a main winding surrounding the core having a central axis and first and second axial ends, a control winding running axially through the core and returning axially outside thereof and a support element surrounding the core for supporting the main winding, said main winding comprising a conductor radially wound above the outside of the support element in a plurality of successive, spaced apart, axially adjacent radial layers, the layers comprising a plurality of turns, each including an inner turn an outer turn and at least one intermediate turn of said conductor wound outwardly onto each other and running successively in an axial direction and having axial spacings between the successive layers, a member located proximate to one of the axial ends of the core for generating a flow of air through the control winding in the core, said support element including means providing air channels communicating with said spacings between the ends of the core, said support means extending axially and partially defined by the radially inner turn of the main winding including a cylindrical wall surrounding the core; a plurality of elongated spacer members between each layer, said spacer members grouped in spaced apart planes corresponding to the spaces between successive layers of turns, each spacer member having a proximal end secured to the cylindrical wall and a free end extending outwardly to the outer turn, said spaced apart layers defining the air channels between the layers; an axially projecting holding member secured to each spacer member and located radially inward of the inner turn and spaced from the cylindrical wall for providing an annular air space therebetween; and wherein said member located proximate to one end of the core generates a flow of air in the air channels through air channels and the annular space for cooling the main winding said support element further comprises an electrically insulating material for electrically screening off an interior portion thereof with respect to said main winding, the interior portion of said cylindrical wall being closed axially at said first end and having a plurality of openings adjacent to said second end for air communication between said interior portion and said air channels outside said core.

14. An inductor according to claim 13, wherein said member for generating a flow of air in said channels produces said flow of air through said openings between said interior portion and said channels.

* * * * *